(12) United States Patent
Huang et al.

(10) Patent No.: US 8,678,137 B2
(45) Date of Patent: Mar. 25, 2014

(54) LUBRICATION MONITORING SYSTEM FOR LINEAR TRANSMISSION DEVICE

(75) Inventors: Yih-Chyun Huang, Taichung (TW); Jenn-Min Lai, Taicung County (TW); Fu-Chun Huang, Taichung County (TW)

(73) Assignee: Hiwin Technologies Corp., Taichung (TW)

( * ) Notice: Subject to any disclaimer, the term of this patent is extended or adjusted under 35 U.S.C. 154(b) by 570 days.

(21) Appl. No.: 12/923,914

(22) Filed: Oct. 14, 2010

(65) Prior Publication Data

US 2012/0037457 A1  Feb. 16, 2012

(51) Int. Cl.
*F16N 27/00* (2006.01)
(52) U.S. Cl.
USPC .......................................... 184/7.4
(58) Field of Classification Search
USPC .......................................... 184/7.4
See application file for complete search history.

(56) References Cited

U.S. PATENT DOCUMENTS 6,179,597 B1   1/2001  Ito et al.
2009/0000592 A1*  1/2009  Luft et al. ................. 123/196 R

FOREIGN PATENT DOCUMENTS

WO  WO 2008/093652 A1  8/2008
WO  WO 2008093652 A1 *  8/2008

* cited by examiner

*Primary Examiner* — Hezron E Williams
*Assistant Examiner* — Gregory J Redmann
(74) *Attorney, Agent, or Firm* — Bacon & Thomas, PLLC

(57) ABSTRACT

A lubrication monitoring system for monitoring the lubricative state of two relatively movable elements of a linear transmission device includes a contact resistance capturing device and a processing unit. The contact resistance capturing device for detecting the contact resistance between the two elements and converting it into a corresponding value. A maximum delay time and a threshold value are preset in the processing unit. A period of time during which the linear transmission device starts to run and then the corresponding value reaches the threshold value defines a delay time. If the specific value of the delay time to the maximum delay time is larger than or equal to a predetermined specific one, it will be judged that the lubrication needs resupply. Therefore, monitoring the lubricative state as the linear transmission device is accelerated can get correct lubricative state to enable correct lubrication resupply.

10 Claims, 7 Drawing Sheets

LUBRICATION MONITORING SYSTEM FOR LINEAR TRANSMISSION DEVICE

BACKGROUND OF THE INVENTION

1. Field of the Invention

The present invention relates generally to how to lubricate a linear transmission device, and more particularly, to a lubrication monitoring system for a linear transmission device.

2. Description of the Related Art

U.S. Pat. No. 6,179,597 disclosed an automatic lubricator for an injection molding machine, characterized in that a lubrication interval Ls of the automatic lubricator is controlled according to length of cycle time S of the injection molding machine. When the cycle time S is longer, the lubrication interval Ls is relatively increased. When the cycle time S is shorter, the lubrication interval Ls is relatively decreased. Besides, the change of temperature is also listed in the conditions as to whether the lubrication is needed or not.

The aforesaid lubrication approach judges whether to lubricate based on the cycle time and the temperature and then lubricates at a predetermined time without considering the actual lubricative state of the linear transmission device. In this way, when the cycle time S is erroneously judged, it may happen that the lubrication is applied when it is not needed or the lubrication is not applied when it is needed.

In addition, PCT Pat. Pub. No. WO 2008/093652 disclosed a lubricative state detector and lubricative state detecting method, in which an electric resistance value detected while the lubrication is sufficient is acted as a threshold preset and a detected electric resistance between the tracker member and the moving block is compared with the threshold preset to judge whether it is necessary to resupply the lubricant according to the current lubricative state.

As indicated above, the aforesaid PCT patent is to compare the electric resistance values under the operation of the linear transmission device. Because the horizontal axis in operation is isokinetically less loaded to have smaller electric resistance value, it cannot indicate that the lubrication is insufficient. For this reason, whether such lubricative state is correct or not is still questionable.

SUMMARY OF THE INVENTION

The primary objective of the present invention is to provide a lubrication monitoring system for a linear transmission device, wherein the lubrication monitoring system can correctly judge the lubricative state.

The secondary objective of the present invention is to provide a lubrication monitoring system for a linear transmission device, wherein the lubrication monitoring system can correctly resupply the lubrication.

The foregoing objectives of the present invention are attained by the lubrication monitoring system, which is to monitor the lubricative state of two relatively movable elements of the linear transmission device, such as but not limited to a lead screw device. The lubrication monitoring system is composed of a contact resistance capturing device and a processing unit. The contact resistance capturing device includes at least two connection ends connected with the two relatively movable elements for detecting the contact resistance between the two elements and outputting a corresponding value according to the detected contact resistance. The processing unit is electrically connected with the contact resistance capturing device. A maximum delay time and a threshold value are preset in the processing unit. The maximum delay time indicates a period of acceleration during which the linear transmission device starts to run and then accelerates to reach a constant speed.

When the surveillance of the lubrication proceeds, the lubricative state can be judged according to the following manners. When the linear transmission device starts to run, the contact resistance capturing device detects the contact resistance alternately and then outputs the corresponding value. A period of time during which the linear transmission device starts to run and then the corresponding value reaches the threshold value defines a delay time, which can be acquired by the processing unit. Next, the processing unit can compare the delay time and the preset maximum delay time. When the specific value of the delay time to the maximum delay time is larger than or equal to a predetermined specific value, it is judged that the lubrication needs resupply and then the processing unit emits a lubrication resupply signal.

DETAILED DESCRIPTION OF PREFERRED EMBODIMENTS

Figure 1:
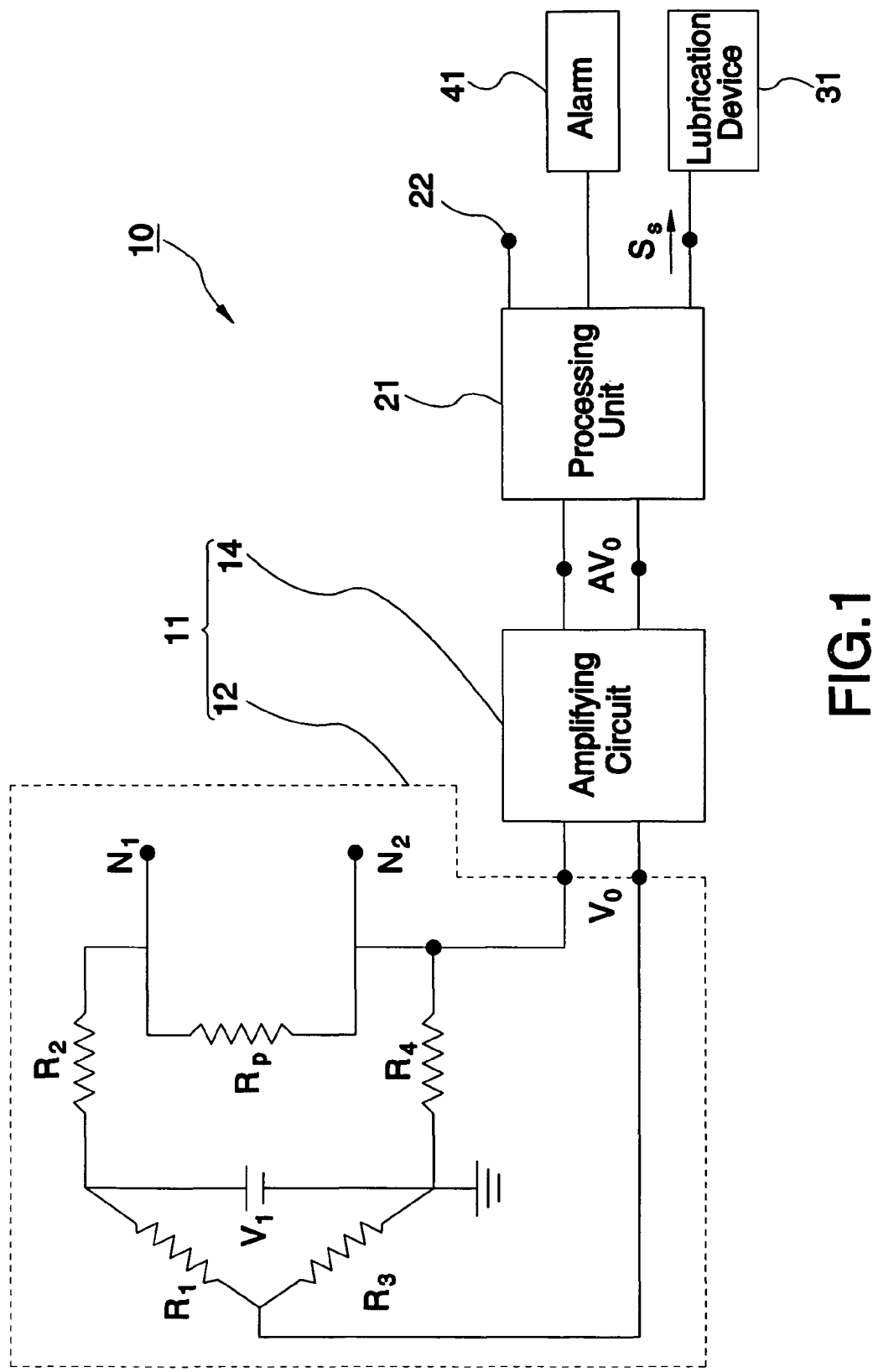
FIG. 1 is a circuit diagram of a first preferred embodiment of the present invention.
Figure 2:
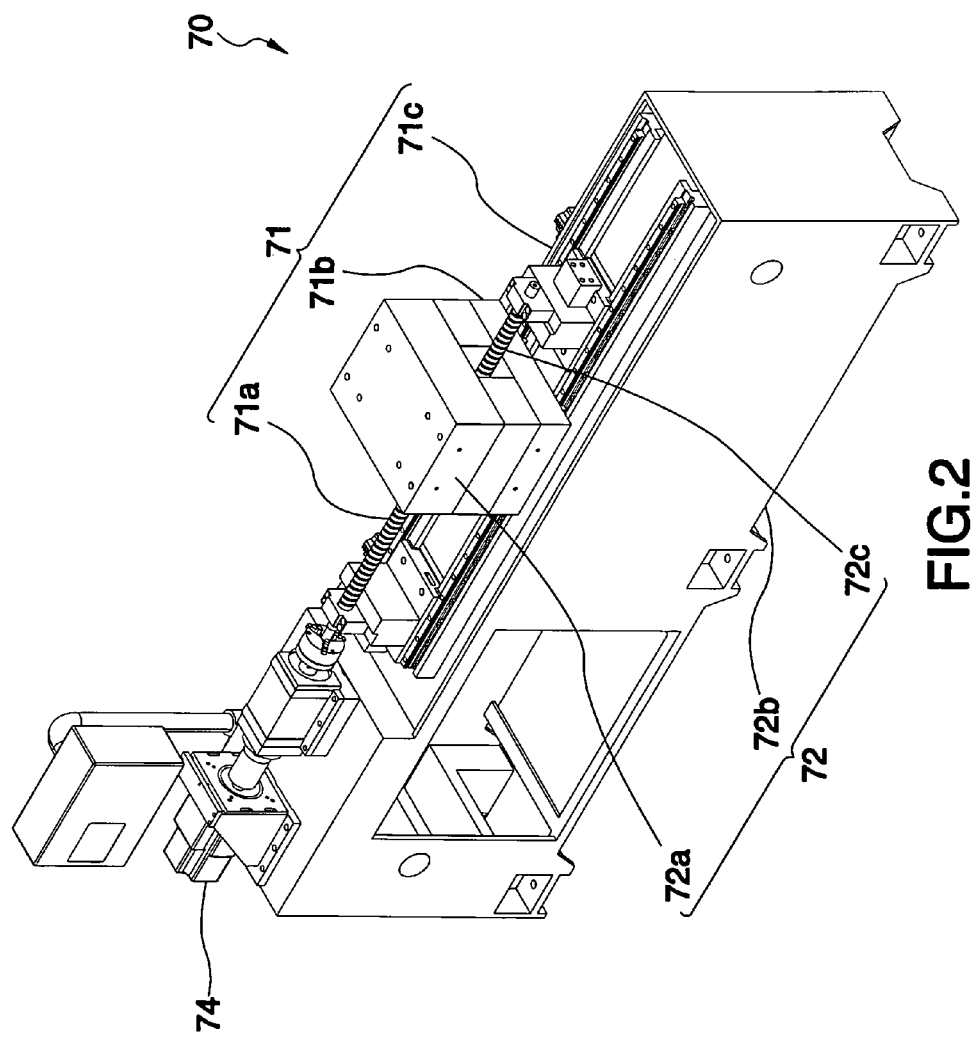
FIG. 2 is a perspective view of the first preferred embodiment of the present invention.

Referring to FIGS. 1-2, a lubrication monitoring system 10 in accordance with a first preferred embodiment of the present invention is to monitor the lubricative state of two relatively movable elements 71 and 72 of a linear transmission device 70. The lubrication monitoring system 10 is composed of a contact resistance capturing device 11 and a processing unit 21. The detailed descriptions and operations of these elements as well as their interrelations are recited in the respective paragraphs as follows.

The contact resistance capturing device 11 includes at least two connection ends N1 and N2 connected with the two elements 71 and 72 for detecting the contact resistance therebetween and outputting a corresponding value $V_c$ according to the detected contact resistance. In this embodiment, the contact resistance capturing device 11 includes a voltage divider circuit 12 and an amplifying circuit 14. The two connection ends N1 and N2 are located on the voltage divider circuit 12 in such a way that the contact resistance detected at the two connection ends N1 and N2 can infer corresponding voltage via the voltage divider circuit 12 and then the voltage is amplified by the amplifying circuit 14 to be the corresponding value $V_c$ for output. Thus, the corresponding value $V_c$ is a voltage value in this embodiment. Besides, the linear transmission device 70 is realized in this embodiment as a lead screw device, and its the two elements 71 and 72, as shown in FIG. 2, can be a set of a screw rod 71a and a platform 72a separately, or a set of a platform 71b and a bench 72b separately, or a set of a bench 71c and a screw rod 72c.

The processing unit 21 is electrically connected with the contact resistance capturing device 11 and preset with a maximum delay time $T_m$, and a threshold value $V_t$. The maximum delay time $T_m$, indicates a period of acceleration, during which the linear transmission device 70 starts to move and accelerates to reach a constant speed. In this embodiment, the threshold value $V_t$ is a voltage value. The processing unit 21 includes a rotational speed receiver terminal 22 for receiving the information about the rotational speed of the linear transmission device 70. Substantially, the rotational speed receiver terminal 22 can be connected with a driving member 74 of the linear transmission device 70 in such a way that the rotational speed of the linear transmission device 70 can be detected by acquiring the signal (voltage signal) of operational speed outputted from the driving member 74. It is not limited to the rotational speed receiver terminal 22 of the processing unit 21 for acquiring the operational speed of the driving member 74 but any other external device connected with the processing unit 21 for receiving the information from the same for detecting the operational speed of driving member 74. In addition, the processing unit 21 can be a single-chip processor, a computer system, a controller, a microprocessor, or a judgment circuit composed of passive elements. In this embodiment, the processing unit 21 is a microprocessor as an example.

Figure 3:
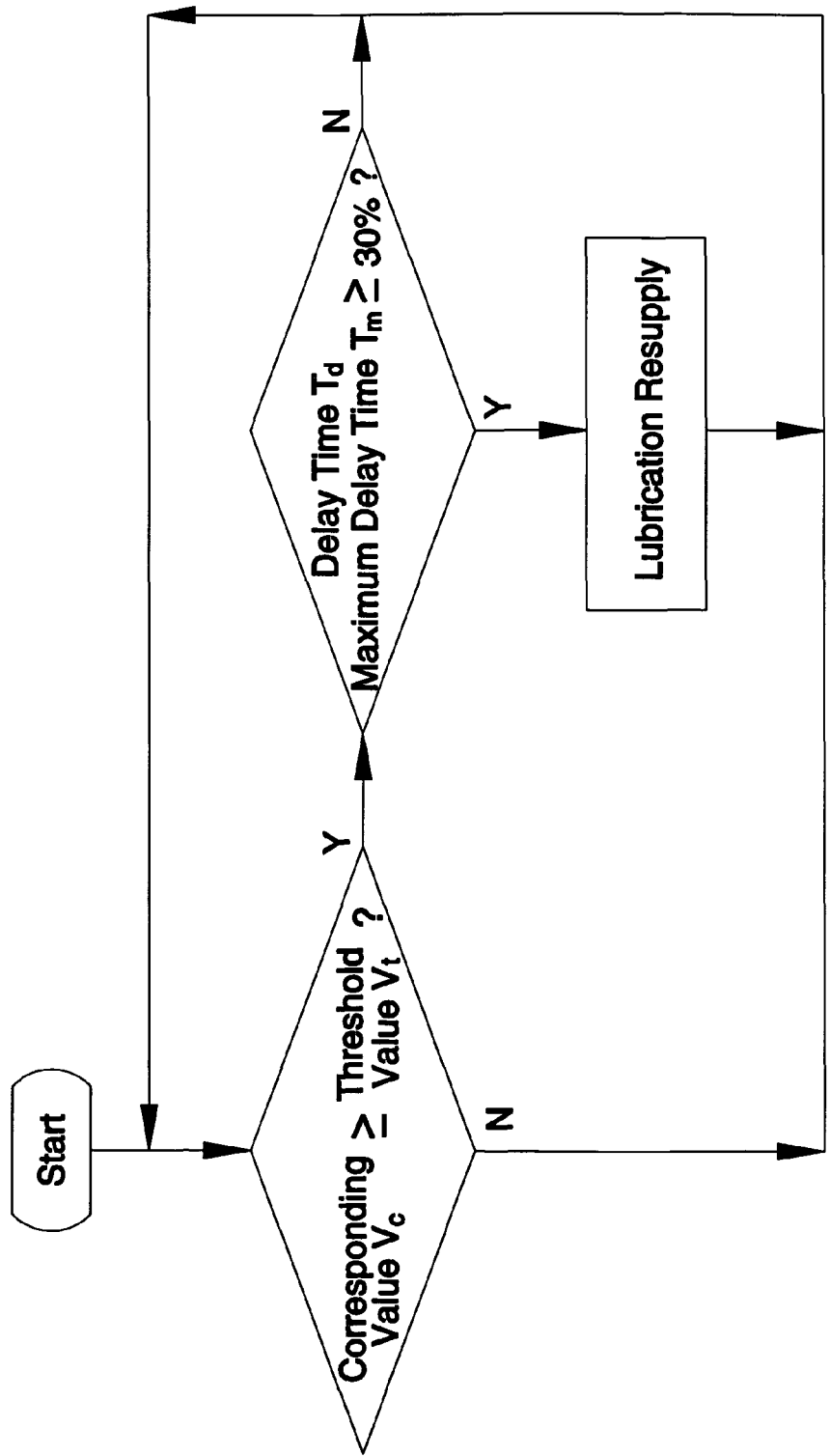
FIG. 3 is a flow chart of the first preferred embodiment of the present invention.

When the lubrication surveillance proceeds, it is based on the following manners in view of FIG. 3.

As the linear transmission device 70 starts to move, the contact resistance capturing device 11 detects contact resistance alternately and outputs the corresponding value $V_c$. A period of time during which the linear transmission device starts to move and then the corresponding value $V_c$ reaches the threshold value $V_t$ defines a delay time $T_d$, which can be acquired by the processing unit 21. If the specific value of the delay time $T_d$ to the maximum delay time $T_m$ is larger than or equal to a predetermined one, it will be judged that the lubrication needs resupply and then the processing unit 21 will emit a lubrication resupply signal S. In this embodiment, the predetermined specific value is 30%; namely, if the delay time $T_d$ is larger than or equal to the maximum delay time $T_m$, for 30%, it will be judged that the lubrication needs resupply. In implementation, the predetermined specific value varies as per the size of the linear transmission device 70. For example, while the smaller linear transmission device 70 is applied, the load is usually smaller, such that the operational speed of the smaller linear transmission device 70 needs less time to be constant, after the operation starts, and the predetermined specific value can be set larger, e.g. 50%; while the bigger linear transmission device 70 is applied, the load is usually larger, such that the operational speed of the smaller linear transmission device 70 needs more time to be constant, after the operation starts, and the predetermined specific value can be set smaller, e.g. 10%.

The processing unit 21 can also be electrically connected with a lubrication device 31, which is a lubricant injection device as an example in this embodiment. After the lubrication resupply signal $S_s$. is transmitted to the lubrication device 31, the lubrication device 31 can inject the lubricant for lubrication resupply.

In addition, the processing unit 21 can be electrically connected with an alarm 41. As the processing unit 21 judges whether the lubrication resupply is needed or not, the alarm 41 can provide premonition with sound, vibration, or lighting to warn that the current lubricative state is insufficient.

Before the linear transmission device 70 works, the processing unit 21 can learn from the rotational speed receiver terminal 22 that the linear transmission device 70 has not worked and thus does not proceed with any detecting or judging actions.

Figure 4:
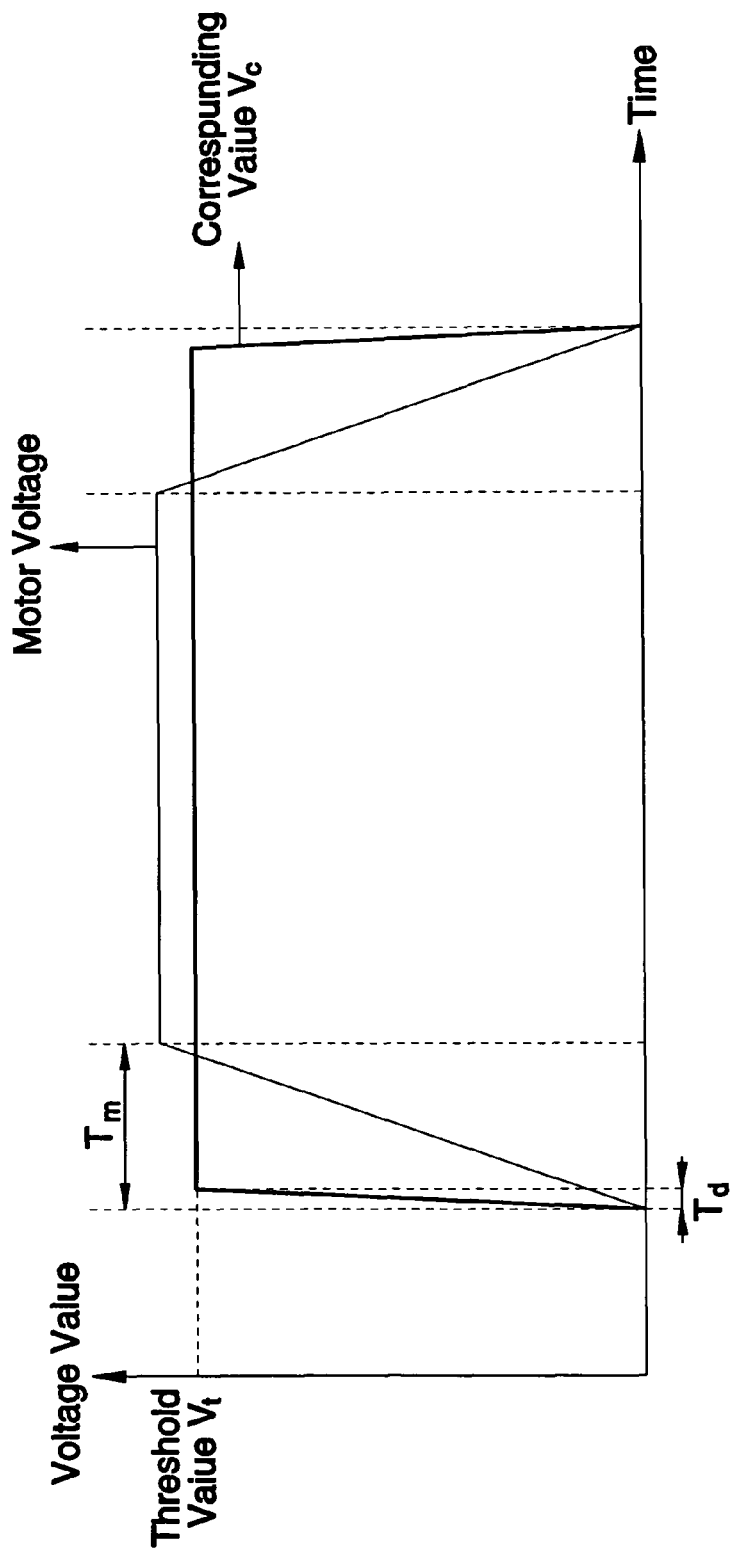
FIG. 4 is an oscillogram of the first preferred embodiment of the present invention, illustrating the status while the lubrication is sufficient.

Referring to FIG. 4, the voltage value of a motor is proportional to the rotational speed of the motor, such that the voltage value of the motor shown stands for the operational speed of the driving member 74. FIG. 4 shows the operational status of the linear transmission device 70 with sufficient lubrication.

Figure 5:
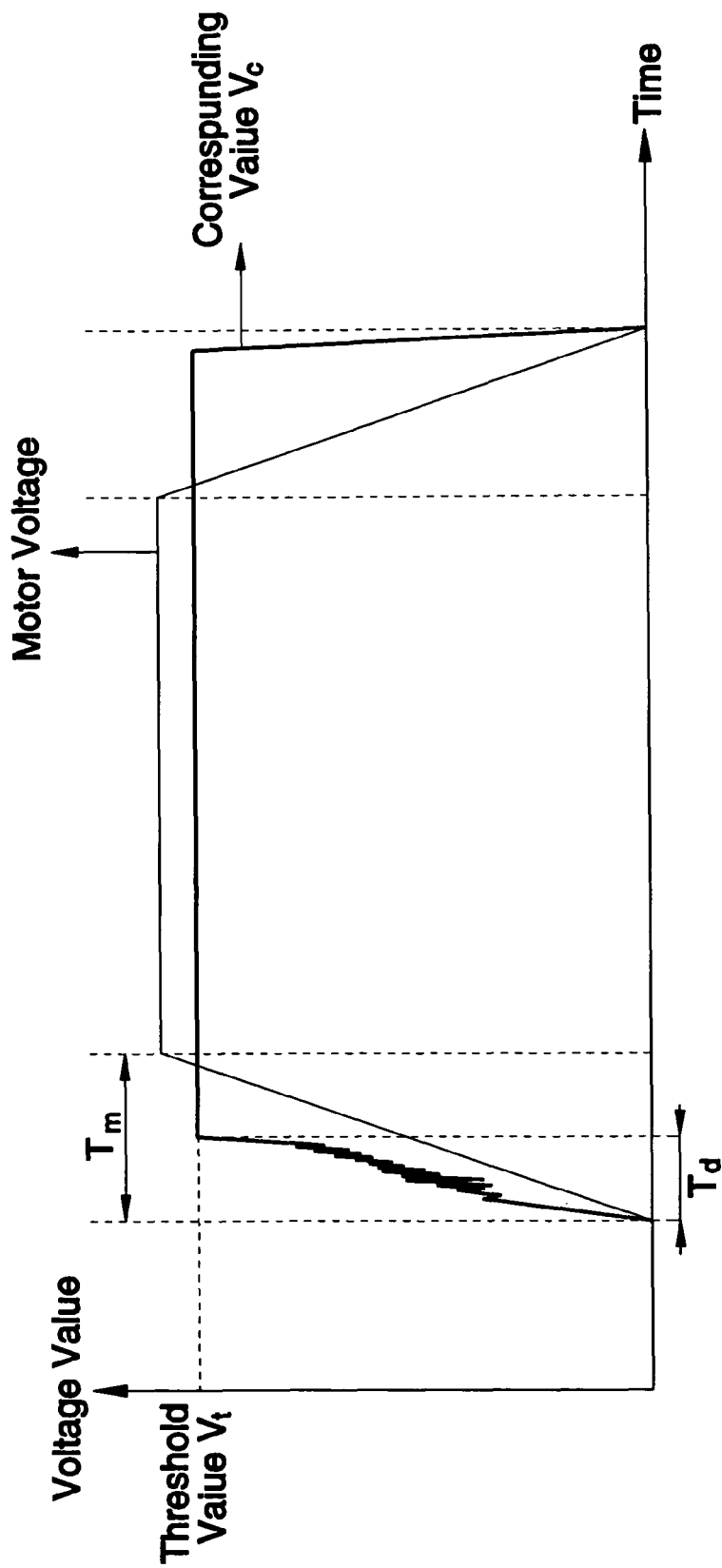
FIG. 5 is a similar to FIG. 4, illustrating the status while the lubrication is insufficient.

Referring to FIGS. 4-5, as the linear transmission device 70 starts to move, the contact resistance capturing device 11 detects the contact resistance of the two elements 71 and 72 alternately, the voltage divider circuit 12 applies voltage division to the contact resistance, and then the amplifying circuit 14 amplifies the same to get the corresponding value $V_c$. Next, the corresponding value $V_c$ is outputted to the processing unit 21 and then the processing unit 21 keeps comparing the corresponding value $V_c$ with the threshold value $V_t$. A period of time during which the linear transmission device starts to move and then the corresponding value $V_c$ reaches (larger than or equal to) the threshold value $V_t$ defines a delay time $T_d$, which cam be acquired by the processing unit 21. Provided the specific value of the delay time $T_d$ to the maximum delay time $T_m$, is smaller than 30%, as shown in FIG. 4, the lubricative state is sufficient. Provided such specific value is larger than 30%, as shown in FIG. 5, the lubricative state is insufficient and thus it is judged that the lubrication resupply is needed. If it is judged that the lubrication resupply is needed, the processing unit 21 will transmit a lubrication resupply signal $S_s$ to the lubrication device 31 and then the lubrication device 31 will inject the lubricant according to lubrication resupply signal S. In addition, the processing unit 21 can further control the alarm 41 for premonition to alert operating personnel that the lubricative state is insufficient.

As can be seen from the above, the first embodiment is to detect the variation of the contact resistance within the period of acceleration and converts the contact resistance into the voltage value for comparison to judge the lubricative state.

Figure 6:
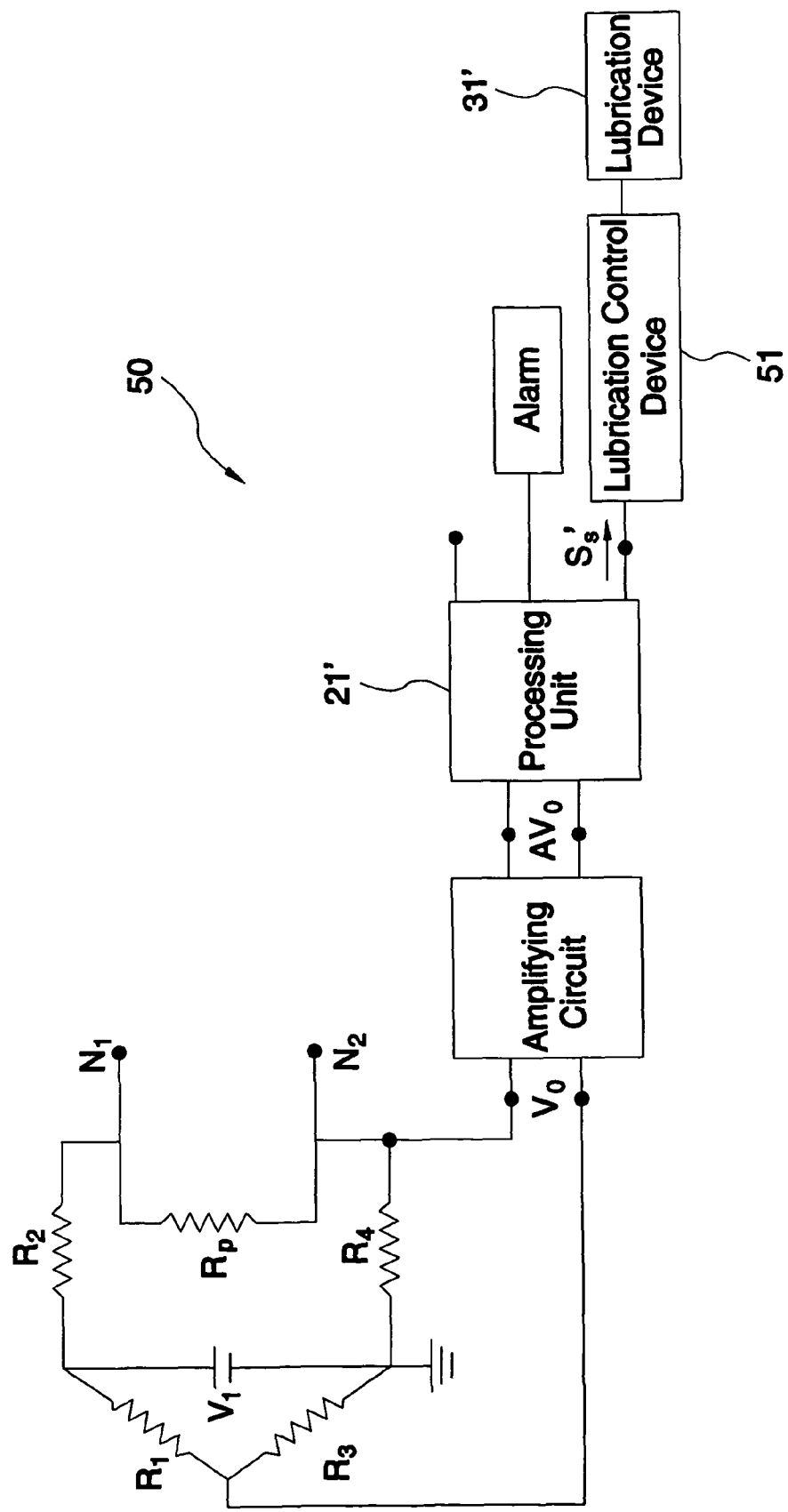
FIG. 6 is a circuit diagram of a second preferred embodiment of the present invention.
Figure 7:
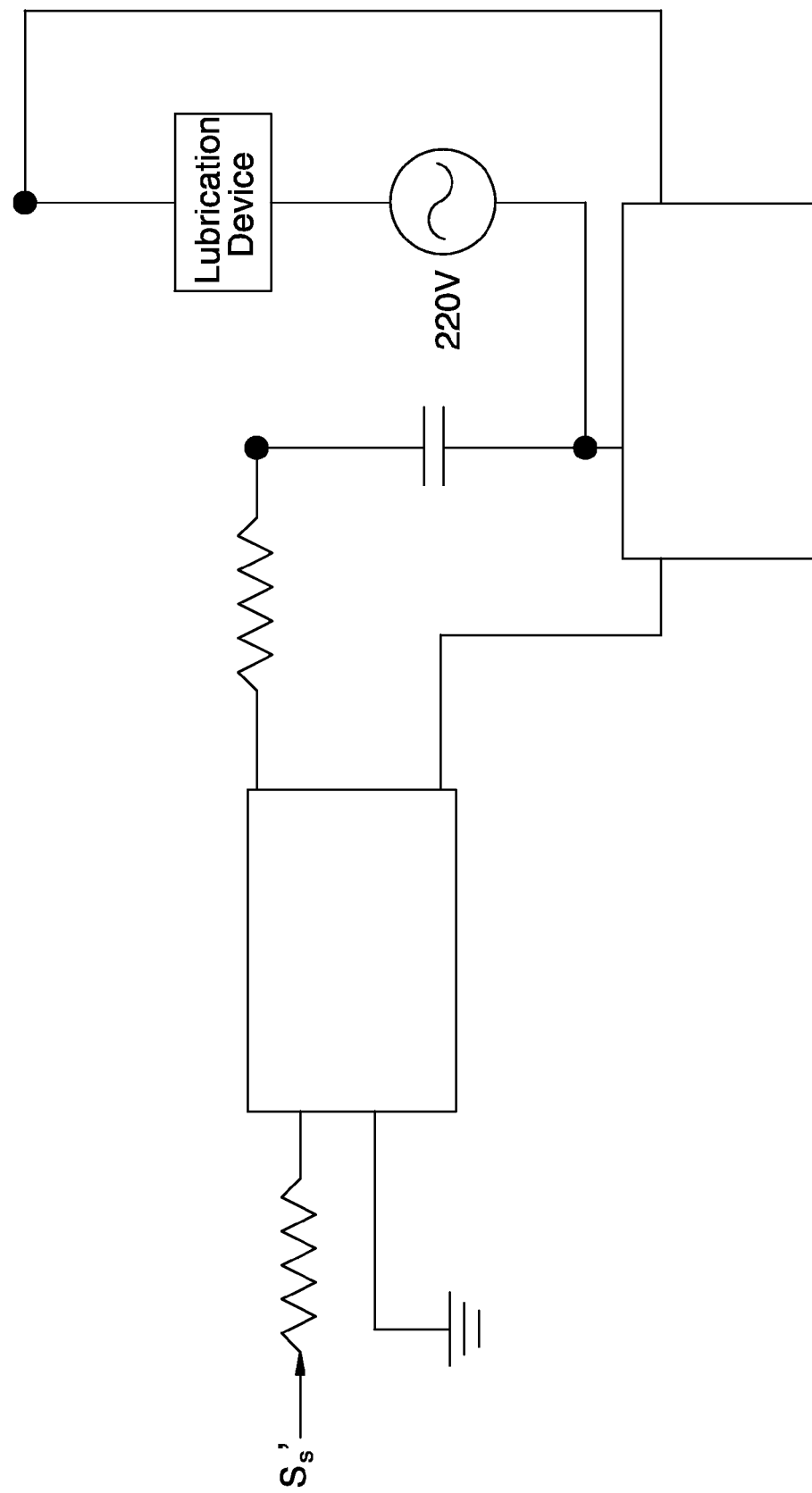
FIG. 7 is another circuit diagram of the second preferred embodiment of the present invention.

Referring to FIGS. 6-7, a lubrication monitoring system 50 in accordance with a second preferred embodiment of the present invention is similar to that of the first embodiment, having the difference recited in the following respective paragraphs.

The lubrication monitoring system 50 further includes a lubrication control circuit 51 electrically connected with the processing unit 21' and the lubrication device 31'. The lubrication resupply signal $S_s$. is transmitted from the processing unit 21' to the lubrication control circuit 51 to indirectly control the lubrication device 31'.

The other operation manners and effects of the second embodiment are identical to those of the first embodiment, so more description is omitted.

It is to be noted that each of the corresponding value $V_c$ and the threshold value $V_t$ is a voltage value in the aforesaid embodiments. However, the corresponding value $V_c$ can also be directly acquired as a resistance value of contact resistance for comparative basis. In the meantime, the threshold value $V_t$ must also be set as a resistance value for the comparison. Although the resistance value is treated as the basis of comparison, it can still be used for acquiring the delay time $T_d$.

In conclusion, the present invention includes the following advantages and effects.

1. When the linear transmission device actually runs, the load as it is accelerated is the maximum and the attrition is also the maximum. Besides, how soon the lubricating film is formed is more important than whether it is formed, so the lubricative state is judged as the linear transmission device is accelerated. Because the linear transmission device seldom runs at the constant speed as it actually works, monitoring the lubricative state as the linear transmission device is accelerated can get the lubricative state more correctly.

2. Correctly judging the lubricative state can make the lubrication resupply more correct to avoid excessive or insufficient lubrication.

Although the present invention has been described with respect to specific preferred embodiments thereof, it is in no way limited to the specifics of the illustrated structures but changes and modifications may be made within the scope of the appended claims.

What is claimed is:

1. A lubrication monitoring system for monitoring the lubricative state of two relatively movable elements of a linear transmission device, comprising:
   a contact resistance capturing device having at least two connection ends connected with the two relatively movable elements for detecting contact resistance therebetween and outputting a corresponding value according to the contact resistance; and
   a processing unit being electrically connected with the contact resistance capturing device, a maximum delay time and a threshold value being preset in the processing unit, the maximum delay time indicating a period of acceleration during which the linear transmission device starts to run and accelerates to reach a constant speed;
   wherein the contact resistance capturing device is configured to, while the linear transmission device starts to run, detect the contact resistance alternately and output the corresponding value;
   wherein the processing unit is configured to determine a delay time according to a period of time from a first time when the linear transmission device starts to run to a second time when the corresponding value reaches a threshold value, and;
   wherein the processing unit is configured to determine if the specific value of the delay time to the maximum delay time is larger than or equal to a predetermined one, and if the specific value of the delay time to the maximum delay time is larger than or equal to a predetermined one, to judge that the lubrication resupply is needed and to emit a lubrication resupply signal.

2. The lubrication monitoring system for monitoring the lubricative state of two relatively movable elements of a linear transmission device as defined in claim 1, wherein the contact resistance capturing device comprises a voltage divider circuit.

3. The lubrication monitoring system for monitoring the lubricative state of two relatively movable elements of a linear transmission device as defined in claim 1, wherein the contact resistance capturing device further comprises an amplifying circuit.

4. The lubrication monitoring system for monitoring the lubricative state of two relatively movable elements of a linear transmission device as defined in claim 1 further comprising an alarm electrically connected with the processing unit.

5. The lubrication monitoring system for monitoring the lubricative state of two relatively movable elements of a linear transmission device as defined in claim 1, wherein both of the corresponding value and the threshold value are resistance values or voltage values.

6. The lubrication monitoring system for monitoring the lubricative state of two relatively movable elements of a linear transmission device as defined in claim 1, wherein the processing unit is electrically connected with a lubrication device; the lubrication resupply signal is transmitted to the lubrication device and then the lubrication control circuit controls the lubrication device according to the lubrication resupply signal for lubrication resupply.

7. The lubrication monitoring system for monitoring the lubricative state of two relatively movable elements of a linear transmission device as defined in claim 6 further comprising a lubrication control circuit electrically connected with the processing unit and the lubrication device, wherein the lubrication resupply signal is transmitted to the lubrication control circuit and then the lubrication control circuit controls the lubrication device for lubrication resupply according to the lubrication resupply signal.

8. The lubrication monitoring system for monitoring the lubricative state of two relatively movable elements of a linear transmission device as defined in claim 6, wherein the processing unit is single-chip processor, a computer system, a controller, a microprocessor, or a judgment circuit composed of at least one passive element.

9. The lubrication monitoring system for monitoring the lubricative state of two relatively movable elements of a linear transmission device as defined in claim 1, wherein the processing unit comprises a rotational speed receiver terminal for receiving the information regarding the rotational speed of the linear transmission device.

10. The lubrication monitoring system for monitoring the lubricative state of two relatively movable elements of a linear transmission device as defined in claim 1, wherein the linear transmission device is a lead screw device.

* * * * *